(12) United States Patent
Walinsky et al.

(10) Patent No.: US 6,645,986 B2
(45) Date of Patent: Nov. 11, 2003

(54) PROCESS FOR THE PREPARATION OF THE MESYLATE SALT TRIHYDRATE OF 1-(4-HYDROXYPHENYL)-2-(4-HYDROXY-4-PHENYLPIPERIDIN-1-YL)-1-PROPANOL

(75) Inventors: Stanley Walter Walinsky, Mystic, CT (US); Terry Gene Sinay, Jr., Preston, CT (US); Joseph Philip Rainville, Uncasville, CT (US)

(73) Assignee: Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/840,580

(22) Filed: Apr. 23, 2001

(65) Prior Publication Data

US 2002/0016465 A1 Feb. 7, 2002

Related U.S. Application Data

(60) Provisional application No. 60/200,673, filed on Apr. 28, 2000.

(51) Int. Cl.[7] .................. A61K 31/445; C07D 211/52
(52) U.S. Cl. ....................................... 514/327; 546/217
(58) Field of Search ........................... 546/217; 514/327

(56) References Cited

U.S. PATENT DOCUMENTS 6,008,233 A * 12/1999 Andino et al. ............... 514/327

OTHER PUBLICATIONS

Andio et al. "preparation of . . . " CA 126:238309 (1997) see RN structure delineation.*
Sigma catalog , p. 649 (1992).*
Merck index, p. 1174–75, (1979).*
CA property file, RN 75–75–2 (1993).*

* cited by examiner

Primary Examiner—Ceila Chang
(74) Attorney, Agent, or Firm—Scully, Scott, Murphy & Presser

(57) ABSTRACT

The present invention is directed to a process for the preparation of the mesylate trihydrate of the (1S,2S)-1-(4-hydroxyphenyl)-2-(4-hydroxy-4-phenylpiperidin-1-yl)-1-propanol compound having the formula (I):

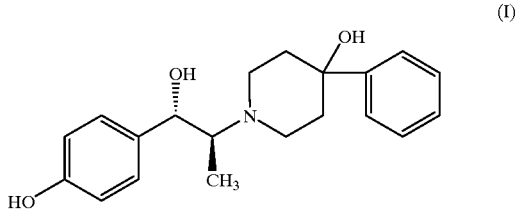

The present invention is also further comprises a process for enantiomeric resolution and isolation of the (D)-(−)-tartrate salt of the compound of the formula (I).

12 Claims, No Drawings

PROCESS FOR THE PREPARATION OF THE MESYLATE SALT TRIHYDRATE OF 1-(4-HYDROXYPHENYL)-2-(4-HYDROXY-4-PHENYLPIPERIDIN-1-YL)-1-PROPANOL

This application claims the benefit of U.S. provisional patent application Ser. No. 60/200,673, filed Apr. 28, 2000.

The present invention is directed to a process for the preparation of the mesylate trihydrate of the compound of formula (I), (1S,2S)-1-(4-hydroxyphenyl)-2-(4-hydroxy-4-phenylpiperidin-1-yl)-1-propanol:

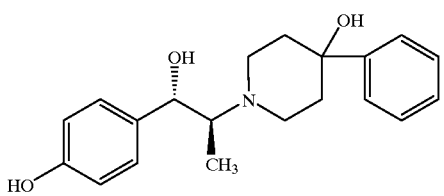

(I)

from its D-(−)-tartrate salt.

The compound of formula (I), (1S,2S)-1-(4-hydroxyphenyl)-2-(4-hydroxy-4-phenylpiperidin-1-yl)-1-propanol, exhibits potent activity as an NMDA (N-methyl-D-aspartic acid) receptor antagonist and is useful in the treatment of epilepsy, anxiety, cerebral ischemia, muscular spasms, multi-infarct dementia, traumatic brain injury, pain, AIDS-related dementia, hypoglycemia, migraine, amyotrophic lateral sclerosis, drug and alcohol addiction, drug and alcohol withdrawal symptoms, psychotic conditions, urinary incontinence and degenerative CNS (central nervous system) disorders such as stroke, Alzheimer's disease, Parkinson's disease and Huntington's disease.

The mesylate trihydrate form of (1S,2S)-1-(4-hydroxyphenyl)-2-(4-hydroxy-4-phenylpiperidin-1-yl)-1-propanol is superior to the anhydrous mesylate as an active therapeutic agent because of its properties. The mesylate trihydrate has a more stable crystalline form than the anhydrous mesylate salt, and hence, a substantially longer shelf life. The trihydrate is also less subject to breakdown in crystal structure due to the inclusion of water in the crystal. U.S. Pat. No. 6,008,233 describes the mesylate salt trihydrate, the anhydrous mesylate salt and free base of (1S,2S)-1-(4-hydroxyphenyl)-2-(4-hydroxy-4-phenylpiperidin-1-yl)-1-propanol, and methods for their preparation.

Further, the free base, the anhydrous mesylate and methods of preparing them are also referred to, generically, in U.S. Pat. No. 5,185,343, which issued on Feb. 9, 1993. Their use in treating certain of the above disorders are referred to, specifically, in U.S. Pat. No. 5,272,160, which issued on Dec. 21, 1993; and International Patent Application PCT/IB 95/00380, which designates the United States, filed on May 18, 1995 and published as WO 96106081. Their use in combination with a compound capable of enhancing and thus restoring the balance of excitatory feedback from the ventral lateral nucleus of the thalamus into the cortex to treat Parkinson's disease is referred to in International Patent Application PCT/IB 95/00398, which designates the United States, filed on May 26, 1995 and published as WO96/37226. The foregoing U.S. patents and patent applications are incorporated herein by reference in their entireties.

SUMMARY OF THE INVENTION

The present invention relates to a process for the preparation of the methanesulfonate trihydrate salt of (1S,2S)-1-(4-hydroxyphenyl)-2-(4-hydroxy-4-phenylpiperidin-1-yl)-1-propanol:

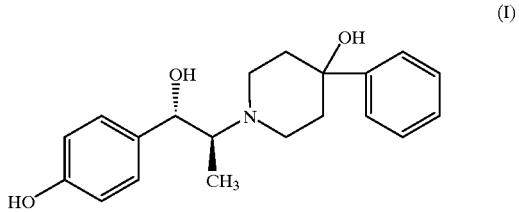

(I)

comprising the steps of
  (i) dissolving the D-(−)-tartrate salt of (1S,2S)-1-(4-hydroxyphenyl)-2-(4-hydroxy-4-phenylpiperidin-1-yl)-1-propanol in an aqueous methanesulfonic acid solution; and
  (ii) allowing the methanesulfonate trihydrate salt to separate out of solution.

In the foregoing process, the molar ratio of methanesulfonic acid to the D-(−)-tartrate salt of (1S, 2S)-1-(4-hydroxyphenyl)-2-(4-hydroxy-4-phenylpiperidin-1-yl)-1-propanol is preferably in the range of 1.3 to 1.0. More preferably, the molar ratio of methanesulfonic acid to the D-(−)-tartrate salt of (1S,2S)-1-(4-hydroxyphenyl)-2-(4-hydroxy-4-phenylpiperidin-1-yl)-1-propanol is in the range of 1.10 to 1.05; most preferably, it is in the range of 1.10 to 1.08.

In the process of the present invention, the aqueous methanesulfonic acid solution of step (i) is preferably created using pyrogen-free water.

The present invention is also directed to any of the above described processes for the preparation of the methanesulfonate trihydrate salt of (1S,2S)-1-(4-hydroxyphenyl)-2-(4-hydroxy-4-phenylpiperidin-1-yl)-1-propanol further comprising the steps of
  (i) dissolving a racemic mixture comprising compounds of formulae (I) and (II):

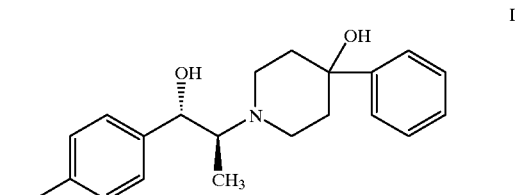

I

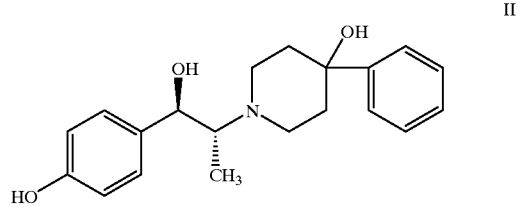

II in aqueous methanol in the presence of D-(−)-tartaric acid; and
  (ii) allowing the D-(−)-tartrate salt of (1S,2S)-1-(4-hydroxyphenyl)-2-(4-hydroxy-4-phenylpiperidin-1- yl)-1-propanol to separate out of solution. In this process, the aqueous methanol preferably has a water content of 5 to 20%. More preferably, embodiment is wherein the aqueous methanol has a water content of 7 to 10%. The present invention is also directed to the process steps of enantiomeric resolution and isolation of the (D)-(−)-tartrate salt of the compound of the formula (I).

The present invention is also directed to the D-(−)-tartrate salt of a compound of formula (I), (1S,2S)-1-(4-hydroxyphenyl)-2-(4-hydroxy-4-phenylpiperidin-1-yl)-1-propanol

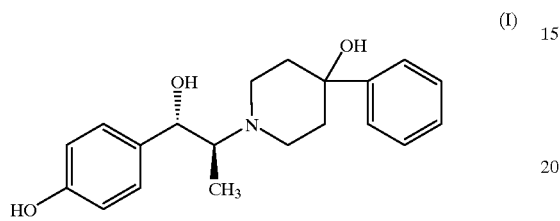

(I)

wherein the ratio of the (1S,2S)-enantiomer to its (1R,2R)-antipode is greater than 97%. More preferably, the ratio of the (1S,2S)-enantiomer to its (1R,2R)-antipode is greater than 98%.

DETAILED DESCRIPTION OF THE INVENTION

The mesylate salt trihydrate of (1S,2S)-1-(4-hydroxyphenyl)-2-(4-hydroxy-4-phenylpiperidin-1-yl)-1-propanol is a white crystalline solid which has a single crystalline form and good solubility in water (25 and 15 mg/mL in pH 3 and 7 aqueous buffered solutions, respectively). The mesylate salt trihydrate is known to form upon allowing the anhydrous mesylate salt to equilibrate in an 81% relative humidity environment. Previous preparations of the mesylate salt trihydrate, e.g., in U.S. Pat. No. 6,008,233, required the use of the free base as the starting material, which required the extra step in the overall synthesis of isolating and drying the free base compound of formula (I) after enantiomeric resolution.

The present invention, however, permits the preparation of the mesylate salt trihydrate directly from the D-(−)-tartrate salt of (1S,2S)-1-(4-hydroxyphenyl)-2-(4-hydroxy-4-phenylpiperidin-1yl)-1-propanol without proceeding via the free base. The D-(−)-tartrate salt used in the foregoing is the product of the enantiomeric resolution of racemic 1-(4-hydroxyphenyl)-2-(4-hydroxy-4-phenylpiperidin-1-yl)-1-propanol. According the present invention permits a more efficient synthesis of the mesylate salt with fewer steps.

The process of the present invention further comprises an improvement in the process for resolving the D-(−)-tartrate salt of (1S,2S)-1-(4-hydroxyphenyl)-2-(4-hydroxy-4-phenylpiperidin-1yl)-1-propanol. Previous processes, e.g., in U.S. Pat. No. 6,008,233, for resolving the racemate of 1-(4-hydroxyphenyl)-2-(4-hydroxy-4-phenylpiperidin-1-yl)-1-propanol involved selective crystallization with optically active tartrate salts from absolute methanol, and almost always required subsequent reslurries and/or recrystallization to achieve an acceptable enantiomeric purity of (1S,2S) 97% or better. The present invention thus provides a means for eliminating repetitive purification steps and greater efficiency in the overall synthetic pathway.

The following reaction Schemes illustrates the process of the present invention.

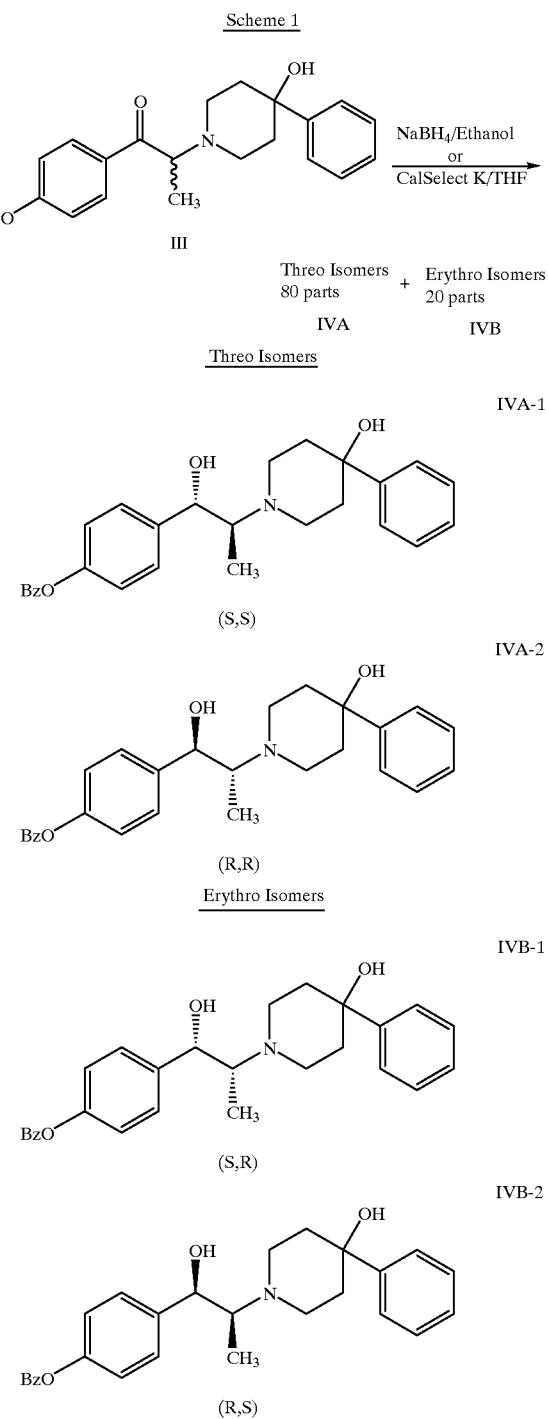

Referring to Scheme 1, the racemic benzyl protected ketone compound of formula (III) is subjected to reduction conditions, either to NaBH$_4$ in ethanol for 6–7 hours at 40 to 50° C. or potassium selectride (CalSelect K) in tetrahydrofuran for 1 to 2 hours at 10 to 20° C., or any other suitable agents and conditions known to those of skill in the art, to produce a mixture of threo and erythro isomers, wherein the threo isomer predominates in a ratio of approximately 80:20 or better in the crude reaction mixture. The ethanol or THF solvents should not contain appreciable amounts of water, i.e., not greater than 0.2 to 0.5% water.

After actual isolation from the solvent, a product of nearly 90% threo orientation, i.e., the threo component being a racemic mixture of compounds of formula (IVA) (i.e., IVA-1 and IVA-2), may be obtained. The starting material of formula (III) is obtained by a procedure disclosed in U.S. Pat. No. 6,008,233, already noted above and incorporated by reference in its entirety.

Referring to Scheme 2, the benzyl group is removed from the racemate of the threo compound of formula (IVA) via any means known to those skilled in the art, preferably via exposure to hydrogenolysis conditions, most preferably, palladium on carbon in the presence of hydrogen gas in wet tetrahydrofuran for approximately 5 to 6 hours at 45 to 50° C. Other effective means of benzyl group removal in a case such as this would be recognized by those of skill in the art.

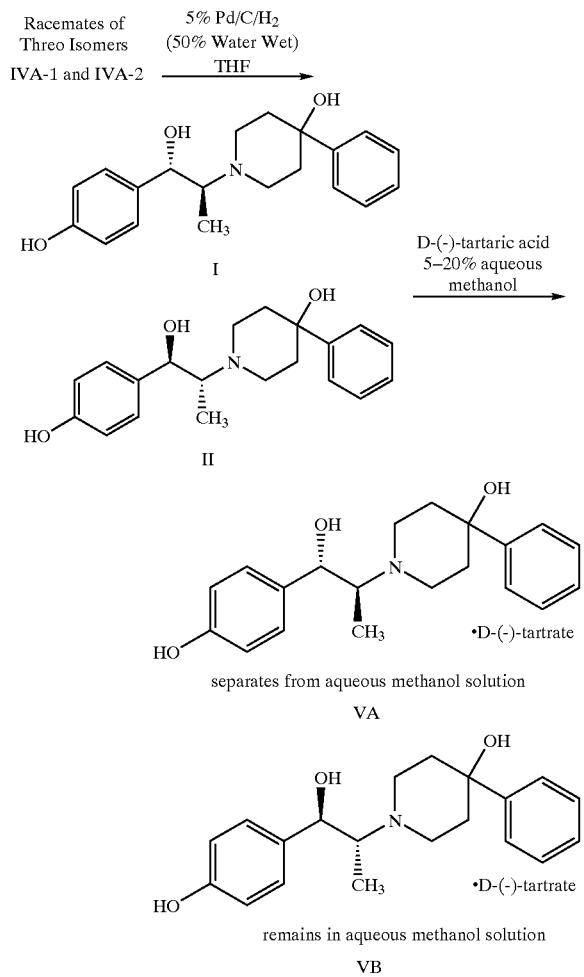

Scheme 2

The product of the foregoing reduction reaction, the racemic mixture of antipodes of the formulae (I) and (II), is then resolved via the formation and selective crystallization of the D-(−)-tartrate salt. The D-(−)-tartrate of (1S,2S)-1-(4-hydroxyphenyl)-2-(4-hydroxy-4-phenylpiperidin-1-yl)-1-propanol (VA) is prepared directly from an absolute methanol solution of the racemate (I and II) by heating the methanolic solution to approximately 50 to 55° C., then slowly adding a solution of D-(−)-tartaric acid in water. The mixture is then heated to approximately 60 to 65° C., and a small amount of D-(−)-tartrate salt of(1S,2S)-1-(4-hydroxyphenyl)-2-(4-hydroxy-4-phenylpiperidin-1-yl)-1-propanol (VA) may optionally be added to promote D-(−)-tartrate salt formation. The mixture is then maintained at reflux temperature (60 to 65° C.) for about four hours during which a thick suspension forms. The slurry is slowly cooled, the solid collected by filtration and washed with methanol. This procedure yields the D-(−)-tartrate salt of (1S,2S)-1-(4-hydroxyphenyl)-2-(4-hydroxy-4-phenylpiperidin- 1-yl)-1-propanol, with 20% or less enantiomeric and diastereomeric impurities. The ratio of water to methanol. i.e. aqueous methanol, should be adjusted to form a final solution within the range of 5 to 20% water/methanol, preferably 7–10%. Table 1 shows the marked improvement in enantiomeric purity of the D-(−)-tartrate salt using aqueous methanol over absolute methanol as solvent. With a procedure utilizing absolute methanol as the solvent, as seen in Table 1, it may require up to two reslurries or recrystallizations to obtain similar levels of enantiomeric purity for the D-(−)-tartrate salt of(1S,2S)-1-(4hydroxyphenyl)-2-(4-hydroxy-4-phenylpiperidin- 1-yl)-1-propanol.

TABLE 1

Resolution of Racemate (Compounds I and II) with D-(−)-Tartaric Acid in Methanol versus Aqueous Methanol

| D-Tartaric Acid Mol equiv. | Solvent (mL/g crude I/II) | Reaction Time | Reaction Temp | Reaction Yield | Re-slurries Required | %-(1R,2R)-Enantiomer |
|---|---|---|---|---|---|---|
| 1.0 | Methanol (20) | 3 h | 65° C. | 78% | 1 | 1.8% |
| 1.0 | Methanol (20) | 3 h | 65° C. | 78% | 1 | 2.0% |
| 1.0 | Methanol (20) | 5 h | 65° C. | 76% | 2 | 1.2% |
| 1.0 | Methanol (20) | 5.5 h | 65° C. | 73% | 2 | 1.7% |
| 1.03 | Methanol (18) Water (1.6) | 3.5 h | 65° C. | 88% | 0 | 2.5% |
| 1.03 | Methanol (18)/ Water (1.6) | 3.5 h | 65° C. | 80% | 0 | 1.1% |

The resolution of racemic 1-(4-hydroxyphenyl)-2-(4-hydroxy4-phenylpiperidin-1-yl)-1-propanol in aqueous methanol to form the D-(−)-tartrate salt of (1S,2S)-1-(4-hydroxyphenyl)-2-(4-hydroxy-4-phenylpiperidin-1-yl)-1-propanol, essentially free of the corresponding (1R,2R) and other diastereomeric isomers, is exemplified in Example 1. Example 2 provides the comparative procedure using absolute methanol as the solvent.

Scheme 3

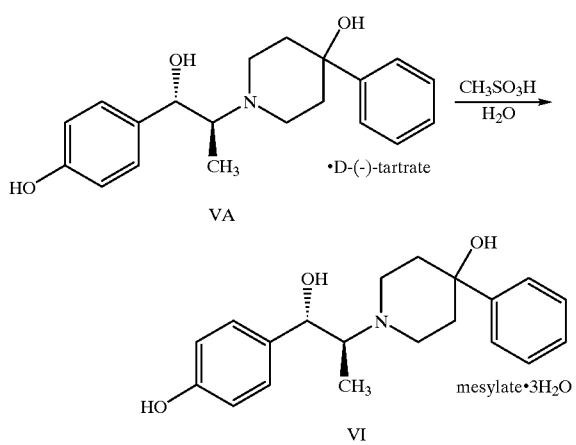

Referring to Scheme 3, the mesylate salt trihydrate of (1S,2S)-1-(4-hydroxyphenyl)-2-(4-hydroxy-4-phenylpiperidin-1-yl)-1-propanol is formed directly from the D-(−)-tartrate salt by dissolving the D-(−)-tartrate salt in water in the presence of 1.00 to 1.15 mole equivalents of methanesulfonic acid, preferably 1.05 to 1.10 mole equivalents, by heating that mixture to approximately 60 to 65° C., then filtering the solution to remove any foreign particulate matter. The warmed solution is then slowly cooled to 15 to 20° C. to yield a thick white suspension, further cooled to 0 to 5° C., and then granulated at 0 to 5° C. for one hour. After isolating the product by filtration, it is then washed with cold water (0 to 5° C.), and the mesylate salt is then dried under an inert atmosphere. Table 2 shows the preparation of the mesylate salt trihydrate conducted over varying ratios of mole equivalents of methanesulfonic acid to (1S,2S)-1-(4-hydroxyphenyl)-2-(4-hydroxy-4-phenylpiperidin-1-yl)-1-propanol.

The mesylate salt trihydrate, similar to the anhydrous mesylate and free base, possesses selective neuroprotective activity, based upon its antiischemic activity and ability to block excitory amino acid receptors. The preferred procedure for evaluating the neuroprotective activity of this compound is that described by Ismail A. Shalaby, et al., *J. Pharm. Exper. Ther.*, 260, 925 (1992). This article is incorporated herein by reference in its entirety and described below.

Cell culture. Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21). Cells are either plated on 96-well microtiter plates at a density of 80,000 cells per well or on 24-well culture plates at a density of 250,000 cells per well. Cultures are grown at 37° C. in a humidified $CO_2$ tissue culture incubator containing 5% $CO_2$/95% air. Proliferation of nonneuronal cells is controlled by adding 20 $\mu$M uridine and 20 $\mu$M 5-fluoro-2-deoxyuridine (Sigma Chemical Co., St. Louis, Mo.) from days 6 to 8 of culture. Culture media is exchanged every 2 to 3 days with fresh stock.

Glutamate toxicity. The cultures are assessed for glutamate toxicity 2 to 3 weeks from initial plating. Culture media is removed and cultures rinsed twice with a CSS (in millimolar.): NaCl, 12-; KCl, 5.4; $MgCl_2$, 0.8; $CaCl_2$, 1.8; glucose, 15; and 4-(2-hydroxyethyl)-1-piperazineethanesulfonic acid, 25 mM (pH 7.4). Cultures are then exposed for 15 minutes (37° C.) to various concentrations of glutamate. After this incubation, cultures are rinsed 3 times with glutamate-free CSS and twice with fresh culture medium without serum. The cultures are then incubated for 20 to 24 hours in serum-free culture medium. The compound being tested is added 2 minutes before and during the 15-minute exposure to glutamate. In some experiments, the compound is added at different times after the glutamate exposure and for the following 20 to 24 hours.

Cell viability is routinely assessed 20 to 24 hours after the excitotoxin exposure by measuring the activity of the cytosolic enzyme LDH. LDH activity is determined from the culture medium of each of the 96 wells of the microtiter plates. A 50-$\mu$l sample of the media is added to an equal volume of sodium-phosphate buffer (0.1 M, pH 7.4) containing 1.32 mM sodium pyruvate and 2.9 mM NADH. The 340 nm absorbance of the total reaction mixture for each of the 96 wells is monitored every 5 seconds for 2 minutes by an automated spectrophotometric microtiter plate reader

TABLE 2

Preparation of Compound of Formula VI from Compound of Formula VA.

| Equivalents | | Water | | Enantiomers | | Diastereomers | |
|---|---|---|---|---|---|---|---|
| Cmpd (VA) (Mol) | $CH_3SO_3H$ (Mol) | Volume (mL/g VA) | Yield Cmpd (VI) | Initial | Final | Initial | Final |
| 1.0 | 1.0 | 3.5 | 89.0% (hazy) | 1.7% | 0.19% | 0.4% | 0.13 |
| 1.0 | 1.05 | 3.5 | 90.4% (hazy) | 1.7% | 0.05% | 0.4% | 0.08 |
| 1.0 | 1.10 | 3.5 | 93.8% | 1.7% | 0.05% | 0.4% | 0.08 |
| 1.0 | 1.15 | 3.25 | 92.4% | 2.5% | 0.07% | 0.2% | — |
| 1.0 | 1.10 | 4.0 | 84.8% | 3.2% | 0.18% | — | <0.1% |
| 1.0 | 1.15 | 3.25 | 87.0% | 4.4% | 0.68% | 0.2% | 0.18 |
| Recrystallization of VI | | 1.5 | 91.9% | 0.68% | 0.1% | 0.18% | 0.02 |

(Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phrase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hours after exposure to 0.1 to 1.0 mM glutamate.

Reagents. DTG can be purchased from Aldrich Chemical Company (Milwaukee, Wis.), and haloperidol from Research Biochemicals Inc. (Natick, Mass.). Spermine can be purchased from Sigma Chemical Co. (St. Louis, Mo.). Horse and fetal bovine serum can be purchased from Hyclone (Logan, Utah). Culture medium, glutamine and penicillin/streptomycin can be purchased from Gibco Co. (Grand Island, N.Y.).

Data analysis. Neurotoxicity can be quantified by measuring the activity of LDH present in the culture medium 20 to 24 hours after glutamate exposure. The increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments is expressed as a percentage of the increase in LDH induced by 1 mM glutamate (or NMDA) for each experiment. Concentrations of NMDA antagonists required to reverse 50% of the LDH increase induced by excitotoxins ($IC_{50}$) are calculated using log-probit analysis from the pooled results of three independent experiments.

The selective neuroprotective antiischemic and excitatory amino acid blocking activities of the mesylate salt trihydrate of this invention render it useful in the treatment of disorders selected from degenerative CNS disorders such as stroke, Alzheimer's disease, Parkinson's disease and Huntington's disease; epilepsy, anxiety, cerebral ischemia, muscular spasms, multiinfarct dementia, traumatic brain injury, pain, AIDS related dementia, hypoglycemia, migraine, amyotrophic lateral sclerosis, drug and alcohol addiction, drug and alcohol withdrawal symptoms, psychotic conditions and urinary incontinence.

In the systemic treatment of such disorders, the dosage is typically from about 0.02 to 250 mg per kg per day (0.001–12.5 g per day in a typical human weighing 50 kg) in single or divided doses, regardless of the route of administration. A more preferred dosage range is from about 0.15 mg per kg per day to about 250 mg per kg per day. Of course, depending upon the exact nature of the illness and the condition of the patient, doses outside this range may be prescribed by the attending physician. The oral route of administration is generally preferred. However, if the patient is unable to swallow, or oral absorption is otherwise impaired, the preferred route of administration will be parenteral (i.m., i.v.) or topical.

The mesylate salt trihydrate may be administered in the form of pharmaceutical compositions together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

The following Examples illustrate the processes of the present invention and the preparation of the compounds of the invention. Melting points are uncorrected. NMR data are reported in parts per million ($\delta$) and are referenced to the deuterium lock signal from the sample solvent (perdeuterodimethylsulfoxide ($d_6$-DMSO), unless otherwise specified). Commercial reagents were utilized without further purification.

EXAMPLE 1

Resolution of 1-(4-Hydroxyphenyl)-2-(4-hydroxy4-phenyl piperidin-1-yl)-1-propanol Using D-(−)-Tartaric Acid in Aqueous Methanol Racemic 1-(4-hydroxyphenyl)-2-(4-hydroxy-4-phenylpiperidin-1-yl)-1-propanol (78.0 kg, 207.7 mol) and absolute methanol (1,223 L) were added to a clean reactor maintained under a nitrogen atmosphere. The mixture was stirred and heated to 50–55° C. After the solution was held at 50–55° C for 1 hour, a solution of D-(−)-tartaric acid (32.1 kg, 214 mol) in water (105 L) was added over 10 minutes. The solution was heated to 60–65° C. and 50 grams of the D-(−)-tartrate salt of (1S,2S)-1-(4-hydroxyphenyl)-2-(4-hydroxy-4-phenylpiperidin-1-yl)-1-propanol in methanol (0.5 L) was added. The solution was maintained at reflux (60–65° C.) for 4 hours during which a thick suspension formed. The slurry was cooled to 30–35° C. over 1.5 hours and then filtered at 30–35° C. The cake was washed with methanol (204 L) and then dried in vacuo at 40–45° C. for 20–30 hours. The D-(−)-tartrate salt of (1S,2S)-1-(4-hydroxyphenyl)-2-(4-hydroxy-4-phenylpiperidin-1-yl)-1-propanol (39.4 kg) was isolated in 40% weight yield (80% of theory). $[\alpha]_D^{25}$+35.2 (0.0185, water). A chiral HPLC showed that the solid contained 1.2% of the (1R,2R)-enantiomer and 0.8% of the (1R,2S)- and (1S,2R)-diastereomers.

EXAMPLE 2

Resolution of 1-(4-Hydroxyphenyl)-2-(4-hvdroxy-4-phenylpiperidin-1-yl)-1-Protanol Using D-(−)-Tartaric Acid in Absolute Methanol To an appropriate flask maintained under a nitrogen atmosphere, 1-(4-hydroxyphenyl)-2-(4-hydroxy-4-phenylpiperidin-1-yl)-1-propanol (189.5 g, 0.58 mol) and methanol (3.8 L) were added. The mixture was heated to 50–55° C. and then D-(−)-tartaric acid (87.0 g , 0.58 mol) was added. The mixture was heated at reflux (~65° C.) for 5 hours. The slurry was cooled at 30–35° C. and then granulated for 1 hour at 30–35° C. The product was filtered and the cake was washed with fresh methanol (135 mL). The wet cake was sampled for a chiral HPLC assay to determine enantiomeric impurity levels. The wet cake was suspended in methanol (1.6 L), and the resulting slurry was heat at reflux (~65° C.) under a nitrogen atmosphere for 5 hours. The slurry was cooled to 30–35° C., granulated for 1 hour at 30–35° C. and then filtered. The filter cake was washed with methanol (136 mL) and then dried in vacuo at 40–45° C. for 18–24 hours. A sample was assayed by chiral HPLC. The D-(−)-tartrate salt of (1S,2S)-1-(4-hydroxyphenyl)-2-(4-hydroxy-4-phenylpiperidin-1-yl)-1-propanol (118.0 g) was obtained in 43% weight yield. At times, as the results show in Table 1 above an additional methanol reslurry is required to decrease the amount of the (1R,2R)-enantiomer impurity below 2.5%.

EXAMPLE 3

Preparation of (1S,2S)-1-(4-Hydroxyphenyl)-2-(4-hydroxy-4-phenylpiperidin-1-yl)-1-propanol Mesylate Trihydrate The D-(−)-tartrate salt of (1S,2S)-1-(4-hydroxyphenyl)-2-(4-hydroxy-4-phenylpiperidin-1-yl)-1-propanol (5.0 g, 10.5 mmol), water (17.5 mL), and methanesulfonic acid (1.05 g, 11.0 mmol) were combined in a 50 mL, 3-neck round bottom flask under a nitrogen atmosphere. The slurry was heated to 60–65° C. to give a solution which was then filtered. The filtrate was slowly cooled over 1 hour to 15–20° C. to give a thick white suspension. The slurry was further cooled to 0–5° C. and then granulated at 0–5° C. for 1 hour. The product was filtered, the cake washed with 2.5 mL of cold water (0–5° C.) and then dried at 20–25° C. under nitrogen sweep. (1S,2S)-1-(4-hydroxyphenyl)-2-(4-hydroxy-4-phenylpiperidin-1-yl)-1-propanol mesylate trihydrate (4.53 g) was isolated in 90.4% overall yield as a white crystalline solid. The physical and chemical properties of the isolated trihydrate were identical to an authentic sample. $^1$H NMR ($d_6$-DMSO) δ9.58 (s, 1H), 8.91 (S, 1H), 7.48 (m, 2H), 7.35 (m, 2,2H), 7.21 (m, 3H), 6.77 (d, J=8.5 Hz, 2H) 6.35 (s, 1H), 5.52 (s, 1H), 4.58 (d, J=8.1 Hz, 1H), 340 (m, 11H) 2.63 (m, 1H), 2.3 (s, 3H), 1.78 (m, 2H), 0.95 (d, J=6.6 Hz, 3H). $^{13}$C NMR ($d_6$-DMSO) δ158.13, 148.61, 132.27, 129.27, 128.80, 127.51, 125.26, 115.89, 72.12, 68.89, 66.30, 47.40, 42.91, 35.71, 35.37. Anal. Calcd. for $C_{20}H_{25}NO_3 \cdot CH_3SO_3H \cdot 3H_2O$: C, 52.81; H, 7.39; N,2.93; S, 6.71. Found: C, 52.77; H, 7.50; N, 2.94; S, 6.96. $\alpha_D$=+54.5° (anhydrous basis).

If low-pyrogen water and pyrogen-free conditions are employed in the above procedure, (1S,2S)-1-(4-hydroxyphenyl)-2-(4-hydroxy-4-phenylpiperidin-1-yl)-1-propanol mesylate trihydrate is suitable for use in the preparation of parenteral drug products. Table 2 reports the preparation of the trihydrate using varying equivalents of methanesulfonic acid. It is notable that when low equivalents of methanesulfonic acid (1.0 to 1.05) are employed, the product trihydrate possesses a residual haze (trace insolubles) when dissolved in water, a property that is unacceptable for parenteral formulations.

What is claimed is:

1. A process forte preparation of the methanesulfonate trihydrate salt of a compound of formula (I):

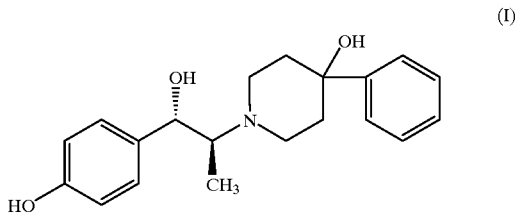

comprising the steps of
   (i) dissolving the D-(−)-tartrate salt of the compound of formula (I) in an aqueous methanesulfonic acid solution; and
   (ii) allowing the methanesulfonate trihydrate salt to separate out of solution.

2. A process according to claim 1 wherein the molar ratio of methanesulfonic acid to D-(−)-tartrate salt of the compound of formula (I) is in the range of 1.3 to 1.0.

3. A process according to claim 1 wherein the molar ratio of methanesulfonic acid to D-(−)-tartrate salt of the compound of formula (I) is in the range of 1.10 to 1.05.

4. A process according to claim 1 wherein the molar ratio of methanesulfonic acid to D-(−)-tartrate salt of the compound of the formula (I) is in the, range of 1.10 to 1.08.

5. A process according to claim 1 wherein the aqueous methanesulfonic acid is created using pyrogen-free water.

6. A process according to claim 1 further comprising the steps of (i) dissolving a racemic mixture comprising compounds of formulae (I) and (II)

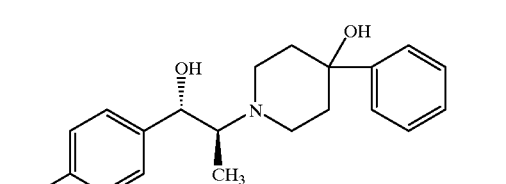

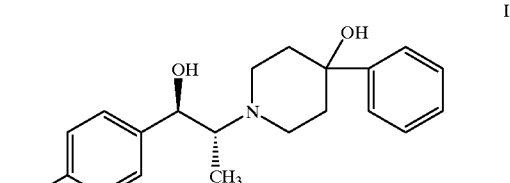

in aqueous methanol in the presence of D-(−)-tartaric acid; and
   (ii) allowing the D-(−)-tartaric salt of the compound of the formula (I) to separate out of solution.

7. A process according to claim 5 wherein the aqueous methanol has a water content of 5 to 20%.

8. A process according to claim 5 wherein the aqueous methanol has a water content of 7 to 10%.

9. A process for the preparation of the D-(−)-tartrate salt of a compound of formula (I):

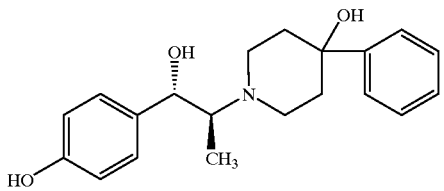
(I)

comprising the steps of (i) dissolving a racemic mixture comprising compounds of formulae (I) and (II)

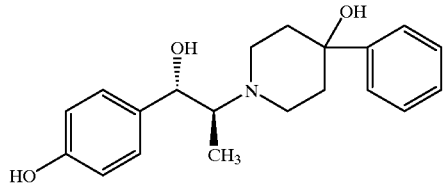
I

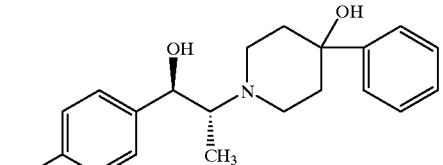
II in an aqueous methanol solution having a water content of 5 to 20% in the presence of D-(−)-tartaric acid; and (ii) allowing the D-(−)-tartrate salt of the compound of formula (I) to separate out of solution.

10. A process according to claim 9 wherein the aqueous methanol has a water content of 7 to 10%.

11. The D-(−)-tartrate salt of a compound of formula (I):

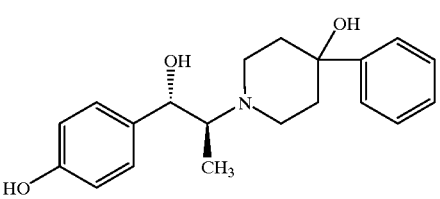
(I)

wherein the ratio of the (1S,2S)-enantiomer to its (1R, 2R)-antipode is greater than 97%.

12. A salt according to claim 11 wherein the ratio of the (1S,2S)-enantiomer to its (1R,2R)-antipode is greater than 98%.

* * * * *